(12) United States Patent
Kulisa et al.

(10) Patent No.: US 9,382,263 B2
(45) Date of Patent: Jul. 5, 2016

(54) THERAPEUTICALLY ACTIVE OXAZOLINE DERIVATIVES

(71) Applicants: UCB Biopharma SPRL, Brussels (BE); KATHOLIEKE UNIVERSITEIT LEUVEN, K.U.Leuven R&D, Leuven (BE)

(72) Inventors: Claire Louise Kulisa, Slough (GB); Daniel Christopher Brookings, Slough (GB); Daniel James Ford, Slough (GB); Richard Jeremy Franklin, Slough (GB); James Thomas Reuberson, Slough (GB); Anant Ramrao Ghawalkar, Uttar Pradesh (IN)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 14/432,842

(22) PCT Filed: Oct. 2, 2013

(86) PCT No.: PCT/EP2013/070600
§ 371 (c)(1),
(2) Date: Apr. 1, 2015

(87) PCT Pub. No.: WO2014/053581
PCT Pub. Date: Apr. 10, 2014

(65) Prior Publication Data
US 2015/0274748 A1 Oct. 1, 2015

(30) Foreign Application Priority Data
Oct. 3, 2012 (GB) .................................. 1217704.4

(51) Int. Cl.
*C07D 495/04* (2006.01)
*A61K 31/424* (2006.01)
*C07D 413/14* (2006.01)

(52) U.S. Cl.
CPC ............ *C07D 495/04* (2013.01); *A61K 31/424* (2013.01); *C07D 413/14* (2013.01)

(58) Field of Classification Search
CPC ... C07D 495/04; C07D 413/14; A61K 31/424
USPC ...................................... 544/250; 514/252.16
See application file for complete search history.

(56) References Cited

U.S. PATENT DOCUMENTS 9,096,614 B2 * 8/2015 Brookings ........... C07D 513/04
9,227,984 B2 * 1/2016 Brookings ........... C07D 495/04

FOREIGN PATENT DOCUMENTS

| WO | 2006/103555 A1 | 10/2006 |
| WO | 2010/103130 A2 | 9/2010 |
| WO | 2011/029054 A1 | 3/2011 |
| WO | 2013/024291 A2 | 2/2013 |

* cited by examiner

*Primary Examiner* — Deepak Rao
(74) *Attorney, Agent, or Firm* — McDonnell Boehnen Hulbert & Berghoff LLP

(57) ABSTRACT

Compounds of formula (I) i.e. monocyclic or bicyclic diamine-substituted thieno[2,3-d]pyrimidine and isothiazolo [5,4-d]pyrimidine derivatives substituted by an optionally substituted oxazolin-2-yl moiety, are beneficial in the treatment and/or prevention of various human ailments, including inflammatory, autoimmune and oncological disorders; viral diseases; and organ and cell transplant rejection.

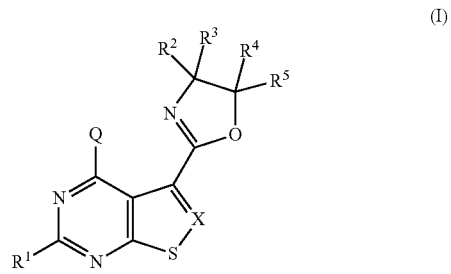

14 Claims, No Drawings

THERAPEUTICALLY ACTIVE OXAZOLINE DERIVATIVES

This application is a US national phase of International Application No. PCT/EP2013/070600 filed on Oct. 2, 2013, which claims priority to Great Britain Patent Application No. 1217704.4 filed on Oct. 3, 2012.

The present invention relates to a class of oxazoline derivatives, and to their use in therapy. These compounds are of benefit as pharmaceutical agents, especially in the treatment of adverse inflammatory, autoimmune and oncological disorders, in the treatment of viral diseases, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2010/103130 describes a family of oxazolo[5,4-d]pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and auto-immune disorders, and organ and cell transplant rejection. WO 2011/147753 discloses the same family of compounds as having significant antiviral activity. Furthermore, WO 2012/035423 discloses the same family of compounds as having significant anticancer activity.

Copending international patent application PCT/GB2012/051992, published on 21 Feb. 2013 as WO 2013/024291, describes a family of monocyclic or bicyclic diamine-substituted thieno[2,3-d]pyrimidine and isothiazolo[5,4-d]pyrimidine derivatives that are stated to be of benefit as pharmaceutical agents, especially in the treatment of adverse inflammatory, autoimmune and oncological disorders, in the treatment of viral diseases, and in the management of organ and cell transplant rejection.

None of the prior art available to date, however, discloses or suggests the precise structural class of oxazoline derivatives as provided by the present invention.

The compounds in accordance with the present invention are active as inhibitors when subjected to the Mixed Lymphocyte Reaction (MLR) test. The MLR test is predictive of immunosuppression or immunomodulation. Thus, when subjected to the MLR test, the compounds of the present invention display an $IC_{50}$ value of 10 µM or less, generally of 5 µM or less, usually of 2 µM or less, typically of 1 µM or less, suitably of 500 nM or less, ideally of 100 nM or less, and preferably of 20 nM or less (the skilled person will appreciate that a lower $IC_{50}$ figure denotes a more active compound).

The present invention provides a compound of formula (I) or an N-oxide thereof, or a pharmaceutically acceptable salt or solvate thereof:

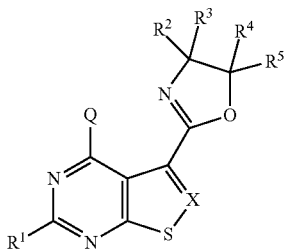

(I)

wherein
Q represents a group of formula (Qa) or (Qb):

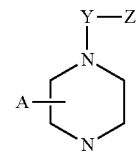

(Qa)

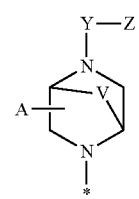

(Qb)

in which the asterisk (*) represents the point of attachment to the remainder of the molecule;

V represents —$CH_2$—, —$C(CH_3)_2$—, —$CH_2CH_2$— or —$CH_2CH_2CH_2$—;

X represents C—$R^6$ or N;

Y represents a covalent bond, or a linker group selected from —C(O)—, —S(O)—, —S(O)$_2$—, —C(O)O—, —C(O)N($R^7$)— and —S(O)$_2$N($R^7$)—;

Z represents hydrogen; or Z represents $C_{1-6}$ alkyl, $C_{3-7}$ cycloalkyl, $C_{3-7}$ cycloalkyl-($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

A represents hydrogen or trifluoromethyl; or A represents $C_{1-6}$ alkyl, optionally substituted by one or more substituents independently selected from halogen, —$OR^a$, —$S(O)R^a$ and —$NR^bR^c$;

$R^1$ represents hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^2$ represents hydrogen or $C_{1-6}$ alkyl; and
$R^3$ represents hydrogen; or $R^3$ represents $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^2$ and $R^3$, when taken together with the carbon atom to which they are both attached, represent $C_{3-7}$ cycloalkyl or $C_{3-7}$ heterocycloalkyl, either of which groups may be optionally substituted by one or more substituents;

$R^4$ represents hydrogen or $C_{1-6}$ alkyl; and
$R^5$ represents hydrogen; or $R^5$ represents $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^4$ and $R^5$, when taken together with the carbon atom to which they are both attached, represent $C_{3-7}$ cycloalkyl or $C_{3-7}$ heterocycloalkyl, either of which groups may be optionally substituted by one or more substituents;

$R^6$ and $R^7$ independently represent hydrogen; or $C_{1-6}$ alkyl, optionally substituted by one or more substituents independently selected from —OR$^a$ and —NR$^b$R$^c$;

$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups, which may comprise benzo-fused analogues thereof, include cyclopropyl, cyclobutyl, cyclopentyl, cyclohexyl, 1,2,3,4-tetrahydronaphthyl and cycloheptyl.

Suitable aryl groups include phenyl and naphthyl, preferably phenyl.

Suitable aryl($C_{1-6}$)alkyl groups include benzyl, phenylethyl, phenylpropyl, phenylbutyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-c]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)⇌enol ($CH=CHOH$) tautomers or amide ($NHC=O$)⇌hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a particular embodiment, Q represents a group of formula (Qa) as defined above. In another embodiment, Q represents a group of formula (Qb) as defined above.

In one embodiment, X represents C—R⁶. In another embodiment, X represents N.

Particular sub-classes of compounds in accordance with the present invention are represented by the compounds of formula (IA), (IB), (IC) and (ID):

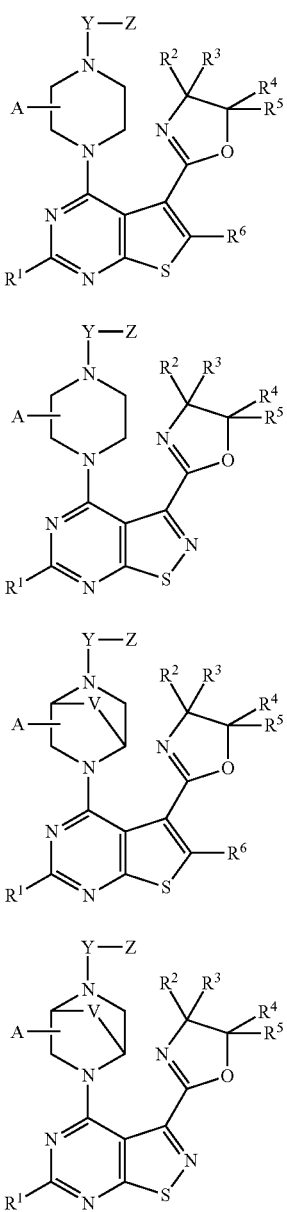

wherein V, Y, Z, A, $R^1$, $R^2$, $R^3$, $R^4$, $R^5$ and $R^6$ are as defined above.

A favoured sub-class of compounds in accordance with the present invention is represented by the compounds of formula (IA) as defined above.

Where Q represents a group of formula (Qa) as defined above, this may be a group of formula (Qa-1) or (Qa-2):

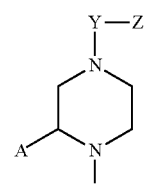

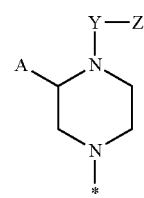

in which the asterisk (*) represents the point of attachment to the remainder of the molecule; and Y, Z and A are as defined above.

In a first embodiment, Q represents a group of formula (Qa-1) as defined above.

In a second embodiment, Q represents a group of formula (Qa-2) as defined above.

In a particular embodiment, V represents —CH₂— or —C(CH₃)₂—. In a first aspect of that embodiment, V represents —CH₂—. In a second aspect of that embodiment, V represents —C(CH₃)₂—. Where V represents —CH₂— or —C(CH₃)₂—, the bicyclic moiety containing the integer V is a 2,5-diazabicyclo[2.2.1]heptane ring system.

In another embodiment, V represents —CH₂CH₂—. Where V represents —CH₂CH₂—, the bicyclic moiety containing the integer V is a 2,5-diazabicyclo[2.2.2]octane ring system.

In a further embodiment, V represents —CH₂CH₂CH₂—. Where V represents —CH₂CH₂CH₂—, the bicyclic moiety containing the integer V is a 6,8-diazabicyclo[3.2.2]-nonane ring system.

Typically, Y represents a covalent bond, or a linker group selected from —C(O)—, —S(O)₂—, —C(O)O—, —C(O)N(R⁷)— and —S(O)₂N(R⁷)—;

Suitably, Y represents a covalent bond, or a linker group selected from —C(O)— and —C(O)N(R⁷)—.

Suitable values of Y include —C(O)—, —S(O)—, —S(O)₂—, —C(O)O—, —C(O)N(R⁷)— and —S(O)₂N(R⁷)—.

Particular values of Y include —C(O)—, —S(O)₂—, —C(O)O—, —C(O)N(R⁷)— and —S(O)₂N(R⁷)—.

Selected values of Y include —C(O)— and —C(O)N(R⁷)—.

In a first embodiment, Y represents a covalent bond. In a second embodiment, Y represents —C(O)—. In a third embodiment, Y represents —S(O)—. In a fourth embodiment, Y represents —S(O)₂—. In a fifth embodiment, Y represents —C(O)O—. In a sixth embodiment, Y represents —C(O)N(R⁷)—. In a seventh embodiment, Y represents —S(O)₂N(R⁷)—.

In one aspect, Z represents hydrogen. In an alternative aspect, Z represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Suitably, Z represents aryl, $C_{3-7}$ heterocycloalkyl or heteroaryl, any of which groups may be optionally substituted by one or more substituents.

In a first embodiment, Z represents hydrogen. In a second embodiment, Z represents $C_{1-6}$ alkyl, which group may be optionally substituted by one or more substituents. In a third embodiment, Z represents $C_{3-7}$ cycloalkyl, which group may be optionally substituted by one or more substituents. In a fourth embodiment, Z represents $C_{3-7}$ cycloalkyl($C_{1-6}$)alkyl, which group may be optionally substituted by one or more substituents. In a fifth embodiment, Z represents aryl, which group may be optionally substituted by one or more substituents. In a sixth embodiment, Z represents aryl($C_{1-6}$)-alkyl, which group may be optionally substituted by one or more substituents. In a seventh embodiment, Z represents $C_{3-7}$ heterocycloalkyl, which group may be optionally substituted by one or more substituents. In an eighth embodiment, Z represents $C_{3-7}$ heterocycloalkyl($C_{1-6}$)alkyl, which group may be optionally substituted by one or more substituents. In a ninth embodiment, Z represents heteroaryl, which group may be optionally substituted by one or more substituents. In a tenth embodiment, Z represents heteroaryl($C_{1-6}$)alkyl, which group may be optionally substituted by one or more substituents.

Selected values of Z include hydrogen; and methyl, cyclopropyl, 1,2,3,4-tetrahydronaphthyl, cyclopentylethyl, phenyl, benzyl, phenylethyl, phenylpropyl, phenylbutyl, pyrrolidinyl, indolinyl, piperidinyl, 1,2,3,4-tetrahydroisoquinolinyl, piperazinylmethyl, morpholinylmethyl, piperazinylethyl, morpholinylethyl, thienyl, indolyl, pyrazolyl, indazolyl, imidazolyl, benzimidazolyl, imidazo[1,2-a]pyridinyl, pyridinyl, quinolinyl, isoquinolinyl, pyrazinyl, quinoxalinyl, thienylmethyl, pyridinylmethyl, furylethyl, indolylethyl, imidazolylethyl, benzimidazolylethyl or pyridinylethyl, any of which groups may be optionally substituted by one or more substituents.

Suitable values of Z include phenyl, indolinyl, thienyl and indolyl, any of which groups may be optionally substituted by one or more substituents.

In a particular embodiment, Z is other than hydrogen.

In one embodiment, Z is unsubstituted. In another embodiment, Z is substituted by one or more substituents, typically by one or two substituents. In one aspect of that embodiment, Z is monosubstituted. In another aspect of that embodiment, Z is disubstituted.

Typical examples of optional substituents on Z include one or more substituents independently selected from halogen, cyano, nitro, $C_{1-6}$ alkyl, trifluoromethyl, aryl, ($C_{1-6}$)alkyl($C_{3-7}$)heterocycloalkyl, ($C_{3-7}$)heterocycloalkyl($C_{1-6}$)alkyl, hydroxy, hydroxy-($C_{1-6}$)alkyl, oxo, $C_{1-6}$ alkoxy, difluoromethoxy, trifluoromethoxy, ($C_{1-3}$)alkylenedioxy, ($C_{1-6}$)alkoxyaryl, aryloxy, haloaryloxy, ($C_{1-6}$)alkoxyaryloxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{2-6}$ alkoxycarbonylamino, N—[($C_{2-6}$)alkoxycarbonyl]-N—[($C_{1-6}$)-alkyl]amino, $C_{1-6}$ alkylsulfonylamino, formyl, $C_{2-6}$ alkylcarbonyl, $C_{3-6}$ cyclo alkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on Z include one or more substituents independently selected from halogen, cyano, $C_{1-6}$ alkyl, $C_{1-6}$ alkoxy, difluoromethoxy, $C_{2-6}$ alkylcarbonyl and $C_{2-6}$ alkoxycarbonyl.

Typical examples of specific substituents on Z include fluoro, chloro, bromo, iodo, cyano, nitro, methyl, isopropyl, trifluoromethyl, phenyl, methylpiperazinyl, piperidinylmethyl, morpholinylmethyl, hydroxy, hydroxymethyl, oxo, methoxy, ethoxy, difluoromethoxy, trifluoromethoxy, methylenedioxy, methoxyphenyl, phenoxy, chlorophenoxy, methoxyphenoxy, methylthio, methylsulfinyl, methylsulfonyl, amino, methylamino, tert-butylamino, dimethylamino, phenylamino, acetylamino, methoxycarbonylamino, N-(tert-butoxycarbonyl)-N-(methyl)amino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on Z include fluoro, iodo, cyano, methyl, methoxy, difluoromethoxy, acetyl and ethoxycarbonyl.

Assorted values of Z include hydrogen, methyl, phenoxymethyl, chlorophenoxymethyl, methoxyphenoxymethyl, dimethylaminomethyl, cyclopropyl, phenylcyclopropyl, methoxyphenylcyclopropyl, 1,2,3,4-tetrahydronaphthyl, cyclopentylethyl, phenyl, fluorophenyl, difluorophenyl, chlorophenyl, (fluoro)(iodo)phenyl, cyanophenyl, methylphenyl, isopropylphenyl, methylpiperazinylphenyl, piperidinylmethylphenyl, morpholinylmethylphenyl, methoxyphenyl, (chloro)(methoxy)phenyl, (methoxy)(methyl)phenyl, dimethoxyphenyl, ethoxyphenyl, difluoromethoxyphenyl, trifluoromethoxyphenyl, methylenedioxyphenyl, dimethylaminophenyl, acetylphenyl, ethoxycarbonylphenyl, benzyl, methylbenzyl, methoxybenzyl, dimethoxybenzyl, methylaminobenzyl, dimethylaminobenzyl, N-(tert-butoxycarbonyl)-N-(methyl)aminobenzyl, phenylethyl, fluorophenylethyl, methylphenylethyl, hydroxyphenylethyl, methoxyphenylethyl, (chloro)(methoxy)phenylethyl, phenylpropyl, phenylbutyl, methylpyrrolidinyl, methylindolinyl, tert-butoxycarbonylpiperidinyl, 1,2,3,4-tetrahydroisoquinolinyl, tert-butoxycarbonyl-1,2,3,4-tetrahydroisoquinolinyl, methylpiperazinylmethyl, morpholinylmethyl, methylpiperazinylethyl, morpholinylethyl, thienyl, indolyl, methylindolyl, pyrazolyl, methylpyrazolyl, indazolyl, methylimidazolyl, benzimidazolyl, imidazo[1,2-a]pyridinyl, pyridinyl, hydroxymethylpyridinyl, quinolinyl, isoquinolinyl, pyrazinyl, quinoxalinyl, thienylmethyl, pyridinylmethyl, furylethyl, indolylethyl, methylimidazolylethyl, benzimidazolylethyl and pyridinylethyl.

Particular values of Z include (fluoro)(iodo)phenyl, cyanophenyl, methylphenyl, methoxyphenyl, (methoxy)(methyl)phenyl, difluoromethoxyphenyl, acetylphenyl, ethoxycarbonylphenyl, methylindolinyl, thienyl and methylindolyl.

One selected value of Z is methoxyphenyl, especially 4-methoxyphenyl.

Another selected value of Z is (methoxy)(methyl)phenyl, especially 4-methoxy-2-methylphenyl.

Suitably, A represents hydrogen or trifluoromethyl; or A represents $C_{1-6}$ alkyl, optionally substituted by —OR$^a$.

Appositely, A represents hydrogen; or A represents $C_{1-6}$ alkyl, optionally substituted by —OR$^a$.

Illustrative values of A include hydrogen, methyl, hydroxymethyl and trifluoromethyl.

Selected values of A include hydrogen, methyl and hydroxymethyl.

In a particular embodiment, A represents hydrogen. In another embodiment, A represents trifluoromethyl. In a further embodiment, A represents $C_{1-6}$ alkyl, optionally substituted by one or more substituents independently selected from halogen, —OR$^a$, —S(O)R$^a$ and —NR$^b$R$^c$. In a first aspect of that embodiment, A represents unsubstituted $C_{1-6}$ alkyl, especially methyl. In a second aspect of that embodiment, A represents $C_{1-6}$ alkyl monosubstituted by halogen, —OR$^a$, —S(O)R$^a$ or —NR$^b$R$^c$. In a third aspect of that embodiment, A represents $C_{1-6}$ alkyl substituted by two substituents independently selected from halogen, —$OR^a$, —$S(O)R^a$ and —$NR^bR^c$. In a particular feature of the second aspect, A represents $C_{1-6}$ alkyl monosubstituted by —$OR^a$, e.g. hydroxymethyl.

Generally, $R^1$ represents hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, aryl, aryl($C_{1-6}$)alkyl, heteroaryl or heteroaryl($C_{1-6}$)alkyl, any of which groups may be optionally substituted by one or more substituents.

Suitably, $R^1$ represents hydrogen, halogen, cyano, nitro, hydroxy, trifluoromethyl, trifluoromethoxy, —$OR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, aryl or heteroaryl, any of which groups may be optionally substituted by one or more substituents.

Typically, $R^1$ represents hydrogen, —$NR^bR^c$ or —$NR^cCOR^d$; or $R^1$ represents $C_{1-6}$ alkyl, which group may be optionally substituted by one or more substituents.

Suitable values of $R^1$ include hydrogen and —$NR^bR^c$.

In one embodiment, $R^1$ represents hydrogen. In another embodiment, $R^1$ represents —$NR^bR^c$. In a further embodiment, $R^1$ represents —$NR^cCOR^d$. In an additional embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$)alkylamino, $C_{2-6}$ alkylcarbonylamino, $C_{2-6}$ alkoxycarbonylamino, aryl($C_{1-6}$)alkoxycarbonylamino, $C_{1-6}$ alkylaminocarbonylamino, arylaminocarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Typical values of $R^2$ include hydrogen, methyl and ethyl. In one embodiment, $R^2$ is hydrogen. In another embodiment, $R^2$ is $C_{1-6}$ alkyl, especially methyl.

Suitably, $R^3$ represents hydrogen; or $R^3$ represents $C_{1-6}$ alkyl, $C_{3-7}$ cycloalkyl or aryl, any of which groups may be optionally substituted by one or more substituents.

Examples of typical substituents on $R^3$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^3$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^3$ include hydrogen, methyl, n-propyl, isopropyl, isobutyl, cyclohexyl and phenyl. Particular values of $R^3$ include hydrogen and methyl.

In one embodiment, $R^3$ is hydrogen. In another embodiment, $R^3$ is $C_{1-6}$ alkyl, especially methyl.

Alternatively, $R^2$ and $R^3$ may together form an optionally substituted spiro linkage. Thus, $R^2$ and $R^3$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^2$ and $R^3$, when taken together with the carbon atom to which they are both attached, may suitably represent an optionally substituted cyclopentyl, cyclohexyl, pyrrolidine or piperidine ring.

Typical values of $R^4$ include hydrogen, methyl and ethyl. In one embodiment, $R^4$ is hydrogen. In another embodiment, $R^4$ is $C_{1-6}$ alkyl, especially methyl.

Suitably, $R^5$ represents hydrogen; or $R^5$ represents $C_{1-6}$ alkyl, $C_{3-7}$ cycloalkyl or aryl, any of which groups may be optionally substituted by one or more substituents.

Examples of typical substituents on $R^5$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^5$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^5$ include hydrogen, methyl, n-propyl, isopropyl, isobutyl, cyclohexyl and phenyl. Particular values of $R^5$ include hydrogen and methyl.

In one embodiment, $R^5$ is hydrogen. In another embodiment, $R^5$ is $C_{1-6}$ alkyl, especially methyl.

Alternatively, $R^4$ and $R^5$ may together form an optionally substituted spiro linkage. Thus, $R^4$ and $R^5$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^4$ and $R^5$, when taken together with the carbon atom to which they are both attached, may suitably represent an optionally substituted cyclopentyl, cyclohexyl, pyrrolidine or piperidine ring, typically an optionally substituted cyclopentyl ring.

Suitably, $R^6$ represents hydrogen or $C_{1-6}$ alkyl.

Suitable values of $R^6$ include hydrogen and methyl.

In one embodiment, $R^6$ represents hydrogen. In another embodiment, $R^6$ represents $C_{1-6}$ alkyl, optionally substituted by one or more substituents independently selected from $-OR^a$ and $-NR^bR^c$. In one aspect of that embodiment, $R^6$ represents unsubstituted $C_{1-6}$ alkyl, especially methyl. In another aspect of that embodiment, $R^6$ represents $C_{1-6}$ alkyl monosubstituted by $-OR^a$ or $-NR^bR^c$. In a further aspect of that embodiment, $R^6$ represents $C_{1-6}$ alkyl substituted by two substituents independently selected from $-OR^a$ and $-NR^bR^c$.

Suitably, $R^7$ represents hydrogen or $C_{1-6}$ alkyl.

Suitable values of $R^7$ include hydrogen and methyl.

In one embodiment, $R^7$ represents hydrogen. In another embodiment, $R^7$ represents $C_{1-6}$ alkyl, optionally substituted by one or more substituents independently selected from $-OR^a$ and $-NR^bR^c$. In one aspect of that embodiment, $R^7$ represents unsubstituted $C_{1-6}$ alkyl, especially methyl. In another aspect of that embodiment, $R^7$ represents $C_{1-6}$ alkyl monosubstituted by $-OR^a$ or $-NR^bR^c$. In a further aspect of that embodiment, $R^7$ represents $C_{1-6}$ alkyl substituted by two substituents independently selected from $-OR^a$ and $-NR^bR^c$.

Typical examples of suitable substituents on $R^a$, $R^b$, $R^c$, $R^d$ or $R^e$, or on the heterocyclic moiety $-NR^bR^c$, include halogen, $C_{1-6}$ alkyl, $C_{1-6}$ alkoxy, difluoromethoxy, trifluoromethoxy, $C_{1-6}$ alkoxy$(C_{1-6})$alkyl, $C_{1-6}$ alkylthio, $C_{1-6}$ alkylsulphinyl, alkylsulphonyl, hydroxy, hydroxy$(C_{1-6})$alkyl, amino$(C_{1-6})$alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di$(C_{1-6})$alkylamino, phenylamino, pyridinylamino, $C_{2-6}$ alkylcarbonylamino, $C_{2-6}$ alkylcarbonylamino$(C_{1-6})$alkyl, $C_{2-6}$ alkoxycarbonylamino, $C_{1-6}$ alkylsulphonylamino, aminocarbonyl, $C_{1-6}$ alkylaminocarbonyl and di$(C_{1-6})$alkylamino carbonyl.

Typical examples of specific substituents on $R^a$, $R^b$, $R^c$, $R^d$ or $R^e$, or on the heterocyclic moiety $-NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Illustratively, $R^a$ represents hydrogen; or $R^a$ represents $C_{1-6}$ alkyl, aryl$(C_{1-6})$alkyl or heteroaryl$(C_{1-6})$alkyl, any of which groups may be optionally substituted by one or more substituents.

Typically, $R^a$ represents $C_{1-6}$ alkyl, aryl, aryl$(C_{1-6})$alkyl, heteroaryl or heteroaryl-$(C_{1-6})$alkyl, any of which groups may be optionally substituted by one or more substituents.

Suitably, $R^a$ represents $C_{1-6}$ alkyl, aryl$(C_{1-6})$alkyl or heteroaryl$(C_{1-6})$alkyl, any of which groups may be optionally substituted by one or more substituents.

Appositely, $R^a$ represents hydrogen; or $R^a$ represents $C_{1-6}$ alkyl, which group may be optionally substituted by one or more substituents.

Particular values of $R^a$ include hydrogen; and methyl, ethyl, benzyl and isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl$(C_{1-6})$alkyl, ideally unsubstituted aryl$(C_{1-6})$alkyl, especially benzyl. In a further embodiment, $R^a$ represents optionally substituted heteroaryl. In a further embodiment, $R^a$ represents optionally substituted heteroaryl$(C_{1-6})$alkyl, e.g. dioxoisoindolylpropyl.

Specific values of $R^a$ include methyl, methoxyethyl, benzyl and dioxoisoindolylpropyl.

Generally, $R^a$ represents hydrogen or $C_{1-6}$ alkyl.

Individual values of $R^a$ include hydrogen and methyl.

In a particular aspect, $R^b$ represents hydrogen or trifluoromethyl; or $R^b$ represents $C_{1-6}$ alkyl, $C_{3-7}$ cycloalkyl, $C_{3-7}$ cycloalkyl$(C_{1-6})$alkyl, aryl, aryl$(C_{1-6})$alkyl, $C_{3-7}$ heterocycloalkyl, $C_{3-7}$ heterocycloalkyl$(C_{1-6})$alkyl, heteroaryl or heteroaryl$(C_{1-6})$alkyl, any of which groups may be optionally substituted by one or more substituents.

Selected values of $R^b$ include hydrogen; and $C_{1-6}$ alkyl, aryl$(C_{1-6})$alkyl, $C_{3-7}$ heterocycloalkyl or $C_{3-7}$ heterocycloalkyl$(C_{1-6})$alkyl, any of which groups may be optionally substituted by one or more substituents.

Appositely, $R^b$ represents hydrogen; or $R^b$ represents $C_{1-6}$ alkyl, which group may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; and methyl, ethyl, n-propyl, tert-butyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-$(C_{1-6})$alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

A particular optional substituent on $R^b$ is hydroxy.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, 1,1-dimethyl-2-hydroxyethyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl. In a further embodiment, $R^b$ represents hydroxy($C_{1-6}$)alkyl, especially 1,1-dimethyl-2-hydroxyethyl.

Particular values of $R^b$ include hydrogen, methyl and 1,1-dimethyl-2-hydroxyethyl.

Selected values of $R^c$ include hydrogen; and $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; and methyl, cyclobutyl, cyclopentyl, cyclohexyl, tetrahydropyranyl or piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, Rd represents optionally substituted $C_{3-7}$ heterocycloalkyl, e.g. thiazolidinyl or oxo-thiazo lidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Generally, $R^d$ represents hydrogen or $C_{1-6}$ alkyl.

Apposite values of $R^d$ include hydrogen and ethyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA), and pharmaceutically acceptable salts and solvates thereof:

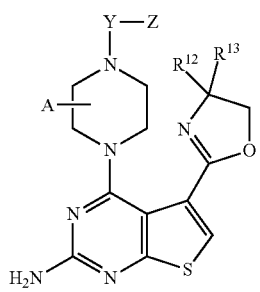

(IIA)

wherein Y, Z and A are as defined above; and $R^{12}$ and $R^{13}$ independently represent hydrogen or $C_{1-6}$ alkyl.

In one embodiment, $R^{12}$ represents hydrogen. In another embodiment, $R^{12}$ represents $C_{1-6}$ alkyl. In one aspect of that embodiment, $R^{12}$ represents methyl.

In one embodiment, $R^{13}$ represents hydrogen. In another embodiment, $R^{13}$ represents $C_{1-6}$ alkyl. In one aspect of that embodiment, $R^{13}$ represents methyl.

Another sub-class of compounds according to the invention is represented by the compounds of formula (IIB), and pharmaceutically acceptable salts and solvates thereof:

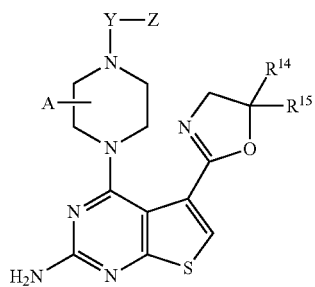

(IIB)

wherein Y, Z and A are as defined above; and $R^{14}$ and $R^{15}$ independently represent hydrogen or $C_{1-6}$ alkyl.

In one embodiment, $R^{14}$ represents hydrogen. In another embodiment, $R^{14}$ represents $C_{1-6}$ alkyl. In one aspect of that embodiment, $R^{14}$ represents methyl. In another aspect of that embodiment, $R^{14}$ represents isopropyl.

In one embodiment, $R^{15}$ represents hydrogen. In another embodiment, $R^{15}$ represents $C_{1-6}$ alkyl. In one aspect of that embodiment, $R^{15}$ represents methyl.

Another sub-class of compounds according to the invention is represented by the compounds of formula (IIC), and pharmaceutically acceptable salts and solvates thereof:

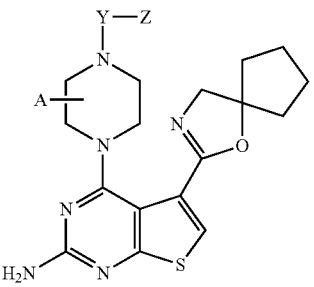

(IIC)

wherein Y, Z and A are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include *Alpharetrovirus, Betaretrovirus, Gammaretrovirus, Deltaretrovirus, Epsilonretrovirus, Lentivirus* and *Spumavirus*. Members of the *Lentivirus* genus include human immunodeficiency virus 1 (HIV-1) and human immunodeficiency virus 2 (HIV-2). Various genera within the Flaviviridae family include *Flavivirus, Pestivirus, Hepacivirus* and Hepatitis G Virus. Members of the Flavivirus genus include Dengue fever virus, yellow fever virus, West Nile encephalitis virus and Japanese encephalitis virus. Members of the *Pestivirus* genus include bovine viral diarrhoea virus (BVDV), classical swine fever virus and border disease virus 2 (BDV-2). Members of the *Hepacivirus* genus include hepatitis C virus (HCV). Members of the Hepatitis G Virus genus include hepatitis G virus. Various genera within the Picornaviridae family include *Aphthovirus, Avihepatovirus, Cardiovirus, Enterovirus, Erbovirus, Hepatovirus, Kobuvirus, Parechovirus, Sapelovirus, Senecavirus, Teschovirus* and *Tremovirus*. Members of the *Enterovirus* genus include poliovirus, coxsackie A virus, coxsackie B virus and rhinovirus. Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises cyclising a compound of formula (III):

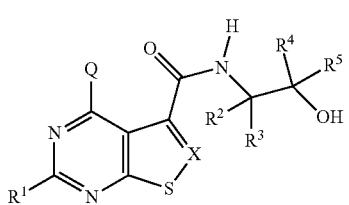

wherein Q, X, $R^1$, $R^2$, $R^3$, $R^4$ and $R^5$ are as defined above.

The cyclisation may be effected by treating compound (III) with 2,3-dichloro-5,6-dicyano-p-benzoquinone (DDQ) and triphenylphosphine, in which case the reaction is conveniently performed at ambient temperature in a suitable solvent or mixture of solvents. Such solvent or solvents may typically be selected as appropriate from a chlorinated solvent such as dichloromethane, and a dipolar aprotic solvent such as N,N-dimethylformamide.

Alternatively, the cyclisation may be effected by treating compound (III) with (methoxycarbonylsulfamoyl)triethylammonium hydroxide (Burgess reagent), in which case the reaction is conveniently performed at ambient temperature in a suitable solvent, e.g. a dipolar aprotic solvent such as N,N-dimethylformamide.

Alternatively, the cyclisation may be effected by a two-step procedure which comprises: (i) reacting compound (III) with a halogenating agent; and (ii) reacting the material thereby obtained with a base.

The halogenating agent of use in step (i) of the above procedure may suitably be thionyl chloride, in which case the process is conveniently effected at an elevated temperature. Alternatively, the halogenating agent may suitably be (diethylamino)sulfur trifluoride (DAST), in which case the process is conveniently effected at a temperature in the region of −78° C. Step (i) may be conveniently performed in a suitable solvent, typically a chlorinated solvent such as dichloromethane.

The base of use in step (ii) of the above procedure may suitably be an alkali metal hydroxide, e.g. sodium hyroxide, in which case the process is conveniently effected at an elevated temperature in a suitable solvent, typically a $C_{1-4}$ alkanol such as methanol. Alternatively, the base may suitably be an alkali metal carbonate, e.g. potassium carbonate, in which case the process is conveniently effected at ambient temperature in a suitable solvent, typically a chlorinated solvent such as dichloromethane.

Alternatively, the compounds of formula (I) above may be prepared by a process which comprises reacting a compound of formula Q-H with a compound of formula (IV):

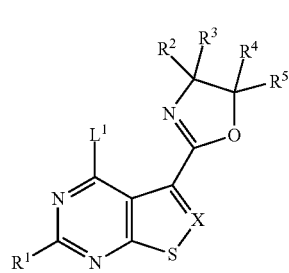

wherein Q, X, $R^1$, $R^2$, $R^3$, $R^4$ and $R^5$ are as defined above, and $L^1$ represents a suitable leaving group.

The leaving group $L^1$ is typically a halogen atom, e.g. chloro.

The reaction is conveniently effected at ambient temperature in a suitable solvent, e.g. a chlorinated solvent such as dichloromethane.

In an alternative procedure, the compounds of formula (I) above wherein Y represents —C(O)—, —S(O)$_2$— or —C(O)O— may be prepared by a process which comprises reacting a compound of formula $L^2$-C(O)—Z, $L^2$-S(O)$_2$—Z or $L^2$-C(O)O—Z respectively with a compound of formula (VA) or (VB):

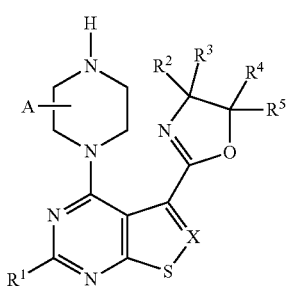

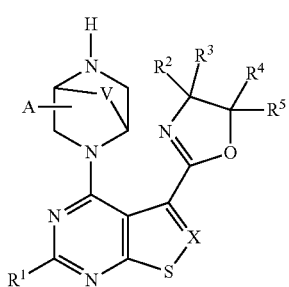

wherein V, X, Z, A, $R^1$, $R^2$, $R^3$, $R^4$ and $R^5$ are as defined above, and $L^2$ represents a suitable leaving group.

The leaving group $L^2$ is typically a halogen atom, e.g. chloro.

The reaction is conveniently effected at ambient temperature in a suitable solvent, e.g. an ethereal solvent such as 1,4-dioxane, typically in the presence of a base. A suitable base for use in the reaction may be an organic base such as N,N-diisopropylethylamine, or an inorganic base such as potassium carbonate.

Alternatively, the leaving group $L^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (VA) or (VB) as defined above with a compound of formula Z—CO$_2$H.

The reaction is conveniently effected at ambient temperature in a suitable solvent, e.g. a dipolar aprotic solvent such as N,N-dimethylformamide, typically in the presence of a coupling agent and a base. A suitable coupling agent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (VA) or (VB) as defined above with an isocyanate derivative of formula Z—N=C=O, wherein Z is as defined above.

The reaction is conveniently effected at ambient temperature in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

In a further procedure, the compounds of formula (I) above wherein Y represents —S(O)$_2$NH— may be prepared by a two-step process which comprises: (i) reacting a compound of formula (VA) or (VB) as defined above with methyl trifluoromethane-sulfonate; and (ii) reacting the material thereby obtained with a compound of formula Z—NH$_2$, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted aryl($C_{1-6}$)alkyl, optionally substituted $C_{3-7}$ heterocycloalkyl($C_{1-6}$)alkyl or optionally substituted heteroaryl($C_{1-6}$)alkyl, may be prepared by a process which comprises reacting a compound of formula (VA) or (VB) as defined above with a compound of formula $Z^1$-$L^3$ wherein $Z^1$ represents $C_{1-6}$ alkyl, $C_{3-7}$ cycloalkyl($C_{1-6}$)alkyl, aryl($C_{1-6}$)alkyl, $C_{3-7}$ heterocycloalkyl($C_{1-6}$)alkyl or heteroaryl($C_{1-6}$)-alkyl, any of which groups may be optionally substituted by one or more substituents, and $L^3$ represents a suitable leaving group.

The leaving group $L^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted aryl($C_{1-6}$)alkyl, optionally substituted $C_{3-7}$ heterocycloalkyl($C_{1-6}$)alkyl or optionally substituted heteroaryl($C_{1-6}$)alkyl, may be prepared by a two-step process which comprises: (i) reacting a compound of formula (VA) or (VB) as defined above with a compound of formula $Z^2$—CHO, wherein $Z^2$—CH$_2$— corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The intermediates of formula (III) above may be prepared by reacting a compound of formula (VI) with a compound of formula (VII):

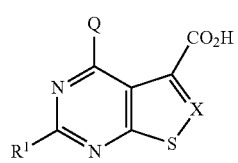

(VI)

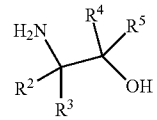

(VII)

wherein Q, X, $R^1$, $R^2$, $R^3$, $R^4$ and $R^5$ are as defined above.

The reaction is conveniently effected at ambient temperature in a suitable solvent, e.g. a dipolar aprotic solvent such as N,N-dimethylformamide, typically in the presence of a coupling agent and a base. A suitable coupling agent for use in the reaction may be HATU. Alternatively, the coupling agent may be 1-(3-dimethylaminopropyl)-3-ethylcarbodiimide hydrochloride (EDC), in which case it will be conveniently utilised in the presence of an additive such as 1-hydroxybenzotriazole hydrate (HOBT). A suitable base for use in the reaction may be an organic base such as N,N-diisopropylethylamine.

The intermediates of formula (VI) above may be prepared by reacting a compound of formula (VIII):

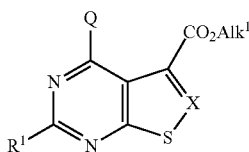

(VIII)

wherein Q, X and $R^1$ are as defined above, and $Alk^1$ represents a $C_{1-6}$ alkyl group, e.g. ethyl; with a base.

The base of use in the above reaction may suitably be an alkali metal hydroxide, e.g. sodium hydroxide. The reaction is conveniently effected at an elevated temperature in a suitable solvent or mixture of solvents. Such solvent or solvents may typically be selected as appropriate from an ethereal solvent such as tetrahydrofuran, and a $C_{1-4}$ alkanol such as ethanol.

The intermediates of formula (VIII) above may be prepared by attaching the —Y—Z moiety to a compound of formula (IXA) or (IXB):

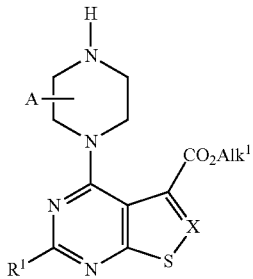
(IXA)

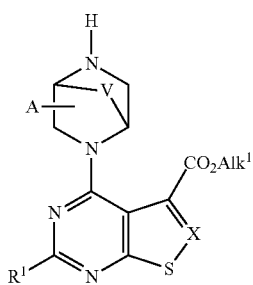
(IXB)

wherein V, X, Y, Z, A, $R^1$ and $Alk^1$ are as defined above; under conditions analogous to those described above for the attachment of the —Y—Z moiety to a compound of formula (VA) or (VB).

The intermediates of formula (IXA) and (IXB) above may be prepared by reacting a compound of formula (X):

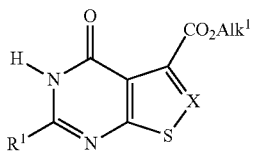
(X)

wherein X, $R^1$ and $Alk^1$ are as defined above; with a compound of formula (XIA) or (XIB):

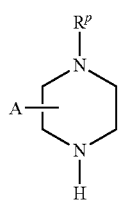
(XIA)

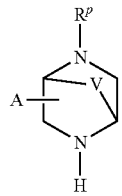
(XIB)

wherein V and A are as defined above, and $R^p$ represents hydrogen or an N-protecting group; followed, as necessary, by removal of the N-protecting group $R^p$.

The N-protecting group $R^p$ is typically tert-butoxycarbonyl (BOC).

The reaction between compound (X) and compound (XIA) or (XIB) is conveniently accomplished at a suitable temperature (ambient or elevated) in a solvent such as acetonitrile or N,N-dimethylformamide, ideally in the presence of a coupling agent such as benzotriazol-1-yloxytris(dimethylamino)phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

Where the N-protecting group $R^p$ is BOC, subsequent removal of the BOC group may typically be accomplished by treatment with an acid, e.g. a mineral acid such as hydrochloric acid, or an organic acid such as trifluoroacetic acid.

The intermediates of formula (VA) and (VB) above may be prepared by cyclising a compound of formula (XIIA) or (XIIB):

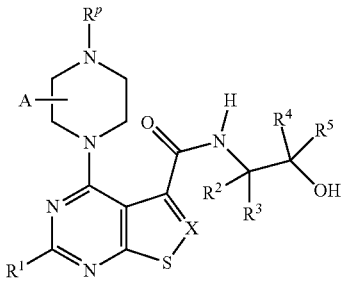
(XIIA)

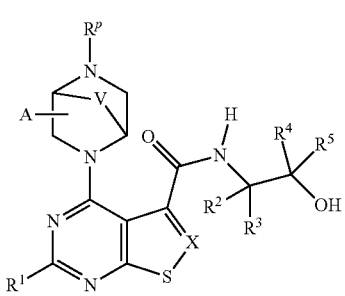
(XIIB)

wherein V, X, A, $R^1$, $R^2$, $R^3$, $R^4$, $R^5$ and $R^p$ are as defined above; under conditions analogous to those described above for the cyclisation of compound (III); followed, as necessary, by removal of the N-protecting group RP, under conditions analogous to those described above.

The intermediates of formula (XIIA) and (XIIB) above may be prepared by reacting a compound of formula (VII) as defined above with a compound of formula (XIIIA) or (XIIIB):

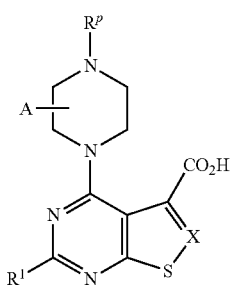

(XIIIA)

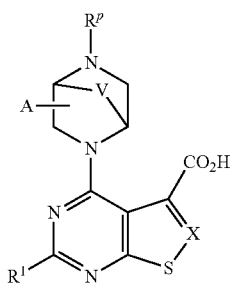

(XIIIB)

wherein V, X, A, $R^1$ and $R^p$ are as defined above; under conditions analogous to those described above for the reaction between compounds (VI) and (VII).

The intermediates of formula (XIIIA) and (XIIIB) above may be prepared by reacting a compound of formula (XIVA) or (XIVB):

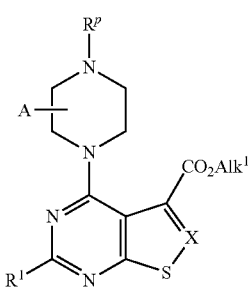

(XIVA)

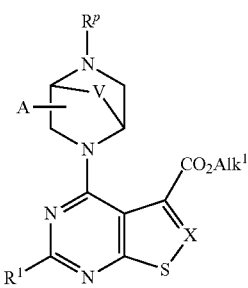

(XIVB)

wherein V, X, A, $R^1$, $R^p$ and $Alk^1$ are as defined above; with a base; under conditions analogous to those described above for the conversion of compound (VIII) into compound (VI).

The intermediates of formula (XIVA) and (XIVB) above may be prepared by reacting a compound of formula (X) with a compound of formula (XIA) or (XIB) as described above.

The intermediates of formula (IV) above wherein $L^1$ represents a halogen atom may be prepared by treating a compound of formula (XV):

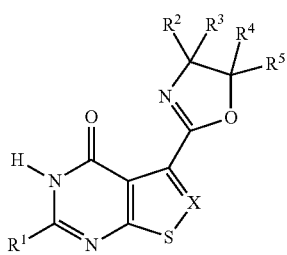

(XV)

wherein X, $R^1$, $R^2$, $R^3$, $R^4$ and $R^5$ are as defined above; with a halogenating agent.

Where $L^1$ in the compounds of formula (IV) is chloro, the halogenating agent employed in the above reaction will be a chlorinating reagent. A suitable chlorinating agent is phosphorus oxychloride.

The reaction is conveniently effected by contacting the reagents at an elevated temperature.

The intermediates of formula (XV) above may be prepared by reacting a compound of formula (VII) as defined above with a compound of formula (XVI):

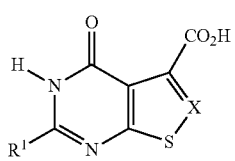

(XVI)

wherein X and $R^1$ are as defined above; under conditions analogous to those described above for the reaction between compounds (VI) and (VII).

The intermediates of formula (XVI) above may be prepared by reacting a compound of formula (X) as defined above with a base, under conditions analogous to those described above for the conversion of compound (VIII) into compound (VI).

Depending upon the substitution pattern around the ring system, the compounds of formula (X), (XV) and (XVI) as depicted above may exist predominantly as the hydroxyimine tautomer.

As will be appreciated, the intermediates of formula (VA) and (VB) correspond to compounds in accordance with the present invention wherein Y represents a covalent bond and Z is hydrogen. Similarly, the intermediates of formula (XIA) and (XIB) wherein $R^p$ is hydrogen correspond to intermediates of formula Q-H wherein Y represents a covalent bond and Z is hydrogen. Furthermore, the intermediates of formula (IXA) and (IXB) correspond to intermediates of formula (XIVA) and (XIVB) wherein $R^p$ is hydrogen.

Where they are not commercially available, the starting materials of formula (VII), (X), (XIA) and (XIB) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, No CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 μCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The IC$_{50}$ was determined from a graph with at least four points, each derived from the mean of 2 experiments. The IC$_{50}$ value represents the lowest concentration of test compound (expressed in μM) that resulted in a 50% inhibition of the MLR.

The compounds of the accompanying Examples were all found to generate IC$_{50}$ values in the MLR test of 10 μM or better.

EXAMPLES

Abbreviations

THF: tetrahydrofuran
MeOH: methanol
EtOH: ethanol
DMSO: dimethylsulfoxide
DIPEA: N,N-diisopropylethylamine
DAST: (diethylamino)sulfur trifluoride
Et$_2$O: diethyl ether
DDQ: 2,3-dichloro-5,6-dicyano-p-benzoquinone
Burgess reagent: (methoxycarbonylsulfamoyl)triethylammonium hydroxide
HATU: O-(7-azabenzotriazol-1-yl)-N,N,N',N'-tetramethyluronium hexafluorophosphate
PyBOP: (benzotriazol-1-yloxy)tripyrrolidinophosphonium hexafluorophosphate
EDC: 1-(3-dimethylaminopropyl)-3-ethylcarbodiimide hydrochloride
h: hour
MS: Mass Spectrometry
HPLC: High Performance Liquid Chromatography
LCMS: Liquid Chromatography Mass Spectrometry
RT: retention time
DMF: N,N-dimethylformamide
DCM: dichloromethane
EtOAc: ethyl acetate
DBU: 1,8-diazabicyclo[5.4.0]undec-7-ene
HOBT: 1-hydroxybenzotriazole hydrate
MeCN: acetonitrile
PPh$_3$: triphenylphosphine
br: broad
M: mass Analytical Methods Unless stated otherwise, the products were analysed using Analytical Method 2.

Method 1: Preparative HPLC (Waters UV Prep System)

The reverse phase separation was carried out on a Waters X-Bridge, C18, 30×150 mm, 10 μm silica particle for both the low and high pH methods.

| Injection Volume | 100-1000 μL |
|---|---|
| UV data | 230 to 400 nm, Resolution 1.2 nm |
| Flow Rate | 50 mL/min | pH 3 Method:

| Solvent A1 | 10 mM ammonium formate in water + 0.1% formic acid |
|---|---|
| Solvent B1 | acetonitrile + 5% Solvent A1 + 0.1% formic acid | pH 10 Method:

| Solvent A2 | 10 mM ammonium bicarbonate in water + 0.1% ammonia solution |
|---|---|
| Solvent B2 | acetonitrile + 5% Solvent A2 + 0.1% ammonia solution |

Analytical Method 2: LCMS (pH 10)

| Column | Waters X-Bridge, 20 x 2.1 mm, 2.5 μL |
|---|---|
| Injection Volume | 1-5 μL |
| UV data | 230 to 400 nm, Peak Width 0.1 s |
| Column Temperature | 40° C. |
| Flow Rate | 1.0 mL/min |
| Split to MS | ~0.05 mL/min |
| Split to DAD and ELSD | ~0.95 mL/min |

High pH (approximately pH 9.5):

| Solvent A2 | 10 mM ammonium bicarbonate in water + 0.1% ammonia solution |
|---|---|
| Solvent B2 | acetonitrile + 5% Solvent A2 + 0.1% ammonia solution |

Analytical Method 3: LCMS (pH 10)

| Column | Waters X-Bridge, 20 x 2.1 mm, 2.5 μL |
|---|---|
| Column ID | E-AC-3/11/COL/035 |
| Mobile Phase A: | 10 mM ammonium formate in water + 0.1% ammonia |
| Mobile Phase B: | acetonitrile + 5% Solvent A + 0.1% ammonia |
| Injection Volume | 5.0 μL |
| Flow Rate | 1.00 mL/minute |

Intermediate 1

Diethyl 2-aminothiophene-3,4-dicarboxylate

To a solution of ethyl pyruvate (1.8 mL, 16 mmol), ethyl cyanoacetate (2.4 mL, 22.4 mmol) and triethylamine (2.7 mL, 19.2 mmol) in DMF (8.0 mL) was added sulfur (564 mg, 17.6 mmol; finely ground using a mortar). The suspension was heated at 60° C. for 5 h. The solvents were removed in vacuo and the slurry was dissolved in EtOAc. The organic solution was extracted successively with brine, saturated aqueous sodium bicarbonate solution, brine, hydrogen chloride (1N) and again brine. The organic fraction was dried over magnesium sulfate after which the solvent was removed in vacuo. The crude residue was purified by silica gel flash chromatography, the mobile phase being a mixture of heptane and EtOAc (in a ratio gradually ranging from 20% to 30% EtOAc in heptane), yielding the title compound (1.8 g) as a yellow powder. $^{13}$C NMR δ (75 MHz, CDCl$_3$) 164.78, 164.30, 162.54, 132.57, 110.81, 104.64, 60.87, 59.83, 13.88, 13.84. MS (m/z) 244 [M+H]$^+$.

Intermediate 2

2-Amino-5-(ethoxycarbonyl)thieno[2,3-d]pyrimidin-4(1H)-one

A mixture of Intermediate 1 (1.0 g, 4.1 mmol), chloroformamidine hydrochloride (1.2 g, 10.3 mmol) and dimethylsulfone (1.9 g, 20.5 mmol) was heated at 135° C. for 45 minutes. Water was added and the mixture was cooled down to room temperature. An aqueous ammonia solution was added to adjust the solution to pH 9. The precipitate was filtered off, yielding the title compound (0.78 g) as a white powder. $^{13}$C NMR δ (75 MHz, CDCl$_3$) 169.24, 163.33, 157.02, 153.90, 129.29, 120.85, 112.43, 60.73, 14.15. MS (m/z) 240 [M+H]$^+$.

Intermediate 3

2-Amino-4-[4-(tert-butoxycarbonyl)piperazin-1-yl]thieno[2,3-d]pyrimidine-5-carboxylic acid ethyl ester DBU (12.1 mL, 79.3 mmol) was added to Intermediate 2 (12.6 g, 52.7 mmol), stirring in acetonitrile (500 mL). After stirring for 5 minutes, PyBOP (36.4 g, 68.5 mmol) was added, followed by tert-butyl piperazine-1-carboxylate (29.4 g, 158 mmol). The reaction mixture was then stirred at room temperature for 12 h, after which time LCMS analysis confirmed disappearance of starting materials. The solid that had formed in the flask was removed by filtration. The filtrate was concentrated in vacuo and the crude residue was purified by column chromatography, eluting with 20-50% EtOAc/hexanes. The title compound (9.5 g) was isolated as a pale solid. δ$_H$ (DMSO-d$_6$, 300 MHz) 7.77 (1H, s), 6.49 (2H, br s), 4.26 (2H, q, J 7.1 Hz), 3.36 (8H, s), 1.41 (9H, s), 1.29 (3H, t, J 7.1 Hz). MS (m/z) 408 [M+H]$^+$.

Intermediate 4 (General Method 1)

2-Amino-4-(piperazin-1-yl)thieno[2,3-d]pyrimidine-5-carboxylic acid ethyl ester, hydrochloric Acid Salt Intermediate 3 (9.5 g) was dissolved in the minimum amount of methanol and HCl (4M in 1,4-dioxane, 20 mL) was added. The reaction mixture was stirred for 1 h, then concentrated in vacuo, to give the title compound (quantitative) as a white solid. LCMS (pH 10) RT 0.99 minutes; MS (m/z) 308 [M+H]$^+$.

Intermediate 5 (General Method 2)

2-Amino-4-[4-(tert-butoxycarbonyl)piperazin-1-yl]thieno[2,3-d]pyrimidine-5-carboxylic acid To a solution of Intermediate 3 (450 mg, 1.1 mol) in EtOH:THF (1:1, 10 mL) was added aqueous NaOH solution (2M, 10 mL). The reaction mixture was heated to 50° C. overnight and on completion (by LCMS monitoring) the solvents were removed in vacuo. The residue was re-dissolved in water, then the solution was adjusted to pH 6 by addition of HCl (2M). The resulting precipitate was filtered and dried on a sinter for 12 h, to give the title compound (380 mg) as a white solid. LCMS (pH 10) RT 0.89 minutes; MS (m/z) 380 [M+H]$^+$.

Intermediate 6 (General Method 3)

4-[2-Amino-5-(2-hydroxy-1,1-dimethylethylcarbamoyl)thieno[2,3-d]pyrimidin-4-yl]-piperazine-1-carboxylic acid tert-butyl ester DIPEA (690 μL, 3.97 mmol) was added to a stirred solution of Intermediate 5 (0.5 g, 1.32 mmol), 2-amino-2-methylpropan-1-ol (140 mg, 1.5 mmol) and HATU (0.75 g, 1.97 mol) in DMF (4 mL). After 15 minutes, the mixture was partitioned between EtOAc and brine. The organic layer was washed with brine, then dried and recrystallised from Et$_2$O. The crystals were filtered, then washed with Et$_2$O and dried on a sinter, to give the title compound (0.59 g) as a cream solid. LCMS (pH 10) RT 1.22 minutes; MS (m/z) 451 [M+H]$^+$.

Intermediate 7

4-[2-Amino-5-(4,4-dimethyl-5H-oxazol-2-yl)thieno[2,3-d]pyrimidin-4-yl]piperazine-1-carboxylic acid tert-butyl ester To a solution of Intermediate 6 (0.54 g, 1.2 mmol), stirring in DMF (6 mL) at 0° C., was added Burgess reagent (0.4 g, 1.68 mmol). The reaction mixture was stirred at room temperature overnight, after which time LCMS analysis showed near completion. A further aliquot of Burgess reagent (0.14 g) was added, and the reaction mixture was stirred for a further 24 h, after which time LCMS analysis showed full conversion to product. The reaction mixture was partitioned between EtOAc and brine. The organic layer was washed with brine, then dried and concentrated in vacuo. The crude residue was purified by column chromatography, eluting with EtOAc/hexane (5:2), followed by recrystallisation from $Et_2O$. The resulting crystals were collected by filtration and dried on a sinter, to give the title compound (0.17 g) as a white solid. LCMS (pH 10) RT 1.37 minutes; MS (m/z) 433 $[M+H]^+$.

Intermediate 8

5-(4,4-Dimethyl-5H-oxazol-2-yl)-4-(piperazin-1-yl)thieno[2,3-d]pyrimidin-2-ylamine Prepared from Intermediate 7 via General Method 1, to give the title compound (quantitative) as a white solid. LCMS (pH 10) RT 0.89 minutes; MS (m/z) 333 $[M+H]^+$.

Intermediate 9 (General Method 4)

2-Amino-4-[4-(4-methoxy-2-methylphenylcarbamoyl)piperazin-1-yl]thieno[2,3-d]-pyrimidine-5-carboxylic acid ethyl ester To Intermediate 4 (4 g, 0.01 mol), stirring in DMF (150 mL), were added 4-methoxy-2-methylphenyl isocyanate (1.5 mL, 0.01 mol) and DIPEA (2 mL, 0.02 mol). The reaction mixture was stirred at room temperature for 15 minutes, then concentrated in vacuo. An aliquot was purified by preparative HPLC, to give the title compound (75 mg) as a white solid; the crude residue was utilised in subsequent steps without further purification. $\delta_H$ (DMSO-$d_6$, 400 MHz) 8.00 (1H, br s), 7.78 (1H, s), 7.03 (1H, d, J 8.6 Hz), 6.77 (1H, m), 6.69 (1H, dd, J 8.4, 2.9 Hz), 6.51 (2H, br s), 4.29 (2H, q, J 7.1 Hz), 3.72 (3H, s), 3.54-3.44 (8H, br m), 2.13 (3H, s), 1.31 (3H, t, J 7.1 Hz). LCMS (pH 10) RT 1.90 minutes; MS (m/z) 471 $[M+H]^+$.

Intermediate 10

2-Amino-4-[4-(4-methoxy-2-methylphenylcarbamoyl)piperazin-1-yl]thieno[2,3-d]-pyrimidine-5-carboxylic acid Prepared from Intermediate 9 (3 g, 6.4 mmol) via General Method 2 to give the title compound (2 g) as a white solid. MS (m/z) 433 $[M+H]^+$.

Intermediate 11

2-Amino-4-[4-(4-methoxyphenylcarbamoyl)piperazin-1-yl]thieno[2,3-d]pyrimidine-5-carboxylic acid ethyl ester Prepared from Intermediate 4 and 4-methoxyphenylisocyanate via General Method 4 to give the title compound as a white solid. $^{13}C$ NMR δ (75 MHz, $CD_3OD$) 171.65, 162.60, 160.54, 159.64, 155.32, 154.73, 133.60, 127.71, 124.13, 121.41 (2C), 113.30 (2C), 106.19, 60.79, 54.73, 47.93 (2C), 43.38 (2C), 13.73. LCMS (pH 10) RT 1.91 minutes; MS (m/z) 457 $[M+H]^+$.

Intermediate 12

2-Amino-4-[4-(4-methoxyphenylcarbamoyl)piperazin-1-yl]thieno[2,3-d]pyrimidine-5-carboxylic acid Prepared from Intermediate 11 via General Method 2 to give the title compound (63%) as a white solid. LCMS (pH 10) RT 0.48 minutes; MS (m/z) 429 $[M+H]^+$.

Intermediates 13 to 22 (General Method 5)

To a solution of Intermediate 10 or Intermediate 12 (0.70 mmol) in DMF (2 mL) was added the appropriate hydroxy-substituted amine (0.84 mmol), followed by HATU (1.05 mmol) and DIPEA (1.05 mmol). The reaction mixture was stirred at room temperature for 12 h. The reaction mixture was then diluted with water and extracted with EtOAc. The organic layer was separated, dried over anhydrous sodium sulphate and concentrated in vacuo. The crude residue was purified by column chromatography (0-10% MeOH:DCM) to afford the title compound.

| | | LCMS | |
|---|---|---|---|
| Intermediate | Compound Name | RT | $(M^+)$ |
| 13 | 2-Amino-4-[4-(4-methoxyphenylcarbamoyl)piperazin-1-yl]thieno[2,3-d]pyrimidine-5-carboxylic acid (2-hydroxyethyl)amide | 1.08 | 472.1 |
| 14 | 2-Amino-4-[4-(4-methoxy-2-methylphenylcarbamoyl)-piperazin-1-yl]thieno[2,3-d]pyrimidine-5-carboxylic acid (2-hydroxyethyl)amide | 1.42 | 486.1 |
| 15 | 2-Amino-4-[4-(4-methoxyphenylcarbamoyl)piperazin-1-yl]thieno[2,3-d]pyrimidine-5-carboxylic acid (1-hydroxycyclopentylmethyl)amide | 1.56 | 526.1 |
| 16 | 2-Amino-4-[4-(4-methoxy-2-methylphenylcarbamoyl)-piperazin-1-yl]thieno[2,3-d]pyrimidine-5-carboxylic acid (1-hydroxycyclopentylmethyl)amide | 1.58 | 540.2 |
| 17 | 2-Amino-4-[4-(4-methoxyphenylcarbamoyl)piperazin-1-yl]thieno[2,3-d]pyrimidine-5-carboxylic acid (2-hydroxypropyl)amide | 1.05 | 486.1 |

|  |  | LCMS | |
|---|---|---|---|
| Intermediate | Compound Name | RT | (M+) |
| 18 | 2-Amino-4-[4-(4-methoxy-2-methylphenylcarbamoyl)-piperazin-1-yl]thieno[2,3-d]pyrimidine-5-carboxylic acid (2-hydroxypropyl)amide | 1.50 | 500.1 |
| 19 | 2-Amino-4-[4-(4-methoxyphenylcarbamoyl)piperazin-1-yl]thieno[2,3-d]pyrimidine-5-carboxylic acid (2-hydroxy-3-methylbutyl)amide | 1.36 | 514.1 |
| 20 | 2-Amino-4-[4-(4-methoxy-2-methylphenylcarbamoyl)-piperazin-1-yl]thieno[2,3-d]pyrimidine-5-carboxylic acid (2-hydroxy-3-methylbutyl)amide | 1.72 | 528.1 |
| 21 | 2-Amino-4-[4-(4-methoxy-2-methylphenylcarbamoyl)-piperazin-1-yl]thieno[2,3-d]pyrimidine-5-carboxylic acid (2-hydroxy-1-methylethyl)amide | 1.47 | 500.1 |
| 22 | 2-Amino-4-[4-(4-methoxyphenylcarbamoyl)piperazin-1-yl]thieno[2,3-d]pyrimidine-5-carboxylic acid (2-hydroxy-1-methylethyl)amide | 1.10 | 486.0 |

Intermediate 23

2-Amino-4-[4-(4-methoxy-2-methylphenylcarbamoyl)piperazin-1-yl]thieno[2,3-d]-pyrimidine-5-carboxylic acid (2-hydroxy-1,1-dimethylethyl)amide To a solution of Intermediate 10 (0.2 g, 0.45 mmol) in DMF (15 mL) were added 2-amino-2-methylpropan-1-ol (68 µL, 1.13 mmol), HOBT (76 mg, 0.50 mmol), EDC (95 mg, 0.50 mmol) and DIPEA (313 µL, 1.80 mmol). The reaction mixture was stirred at room temperature overnight, then concentrated in vacuo. The crude material was purified by column chromatography, eluting with 0-10% MeOH/EtOAc, to give the title compound (135 mg) as a white solid. $\delta_H$ (DMSO-$d_6$, 400 MHz) 8.00 (1H, s), 7.67 (1H, s), 7.36 (1H, s), 7.03 (1H, d, J 8.6 Hz), 6.77 (1H, m), 6.69 (1H, dd, J 8.6, 2.9 Hz), 6.40 (2H, br s), 4.89 (1H, t, J 5.8 Hz), 3.72 (3H, s), 3.48 (8H, br m), 3.31 (6H, s), 2.12 (2H, s), 1.31 (3H, s). LCMS (pH 10) RT 1.28 minutes; MS (m/z) 514 [M+H]+.

Example 1

4-[2-Amino-5-(4,4-dimethyl-5H-oxazol-2-yl)thieno[2,3-d]pyrimidin-4-yl]piperazine-1-carboxylic acid (4-methoxy-2-methylphenyl)amide DDQ (33 mg, 0.15 mmol) and PPh$_3$ (38 mg, 0.15 mmol) were stirred in DCM (10 mL) in an oven-dried flask for 3 minutes, followed by the addition of Intermediate 23 (50 mg, 0.09 mmol). A yellow precipitate formed and a few drops of DMF were added to aid solubility. The reaction mixture was left to stir overnight. The reaction failed to reach completion, but the title compound (11 mg) was isolated as a white solid by preparative HPLC (Analytical Method 1). $\delta_H$ (DMSO-$d_6$, 400 MHz) 7.99 (1H, br s), 7.55 (1H, br s), 7.03 (1H, br d, J 8.3 Hz), 6.77 (1H, br s), 6.70 (1H, br d, J 7.1 Hz), 6.44 (2H, br s), 4.10 (2H, br s), 3.72 (3H, br s), 3.52 (4H, br m), 3.46 (4H, br m), 2.12 (3H, br s), 1.31 (6H, br s). LCMS (pH 10) RT 2.26 minutes; MS (m/z) 496 [M+H]+.

Examples 2 to 11 (General Method 6)

The appropriate isocyanate (1.5 equiv., 0.12 mmol) was added to a reaction tube. A solution of Intermediate 8 (300 mg) in DMF (10 mL) and DIPEA (0.28 mL) was prepared and an aliquot of this solution (1 mL) was added to the tube. The tube was covered with parafilm and stirred overnight at room temperature. The reaction mixture was analysed by LCMS, then filtered through an acrodisk into a HPLC submission vial, washing with DMF (0.2 mL) into a second vial. The reaction mixture was purified using Analytical Method 1. The product fraction was evaporated, then transferred in MeCN/water to a submission vial and freeze-dried, to give the title compound as a white solid.

|  |  |  | LCMS | |
|---|---|---|---|---|
| Example | Compound Name | Method | RT | (M+) |
| 2 | 4-[2-Amino-5-(4,4-dimethyl-5H-oxazol-2-yl)thieno-[2,3-d]pyrimidin-4-yl]-N-(4-methoxyphenyl)-piperazine-1-carboxamide | 2 | 1.68 | 482.8 |
| 3 | 4-[2-Amino-5-(4,4-dimethyl-5H-oxazol-2-yl)thieno-[2,3-d]pyrimidin-4-yl]-N-(2-fluoro-4-iodophenyl)-piperazine-1-carboxamide | 2 | 2.10 | 596.6 |
| 4 | 4-[2-Amino-5-(4,4-dimethyl-5H-oxazol-2-yl)thieno-[2,3-d]pyrimidin-4-yl]-N-(2-cyanophenyl)piperazine-1-carboxamide | 2 | 1.74 | 477.8 |
| 5 | Ethyl 4-({4-[2-amino-5-(4,4-dimethyl-5H-oxazol-2-yl)thieno[2,3-d]pyrimidin-4-yl]piperazine-1-carbonyl}amino)benzoate | 2 | 1.96 | 524.8 |
| 6 | N-(4-Acetylphenyl)-4-[2-amino-5-(4,4-dimethyl-5H-oxazol-2-yl)thieno[2,3-d]pyrimidin-4-yl]piperazine-1-carboxamide | 2 | 1.66 | 494.8 |
| 7 | 4-[2-Amino-5-(4,4-dimethyl-5H-oxazol-2-yl)thieno-[2,3-d]pyrimidin-4-yl]-N-(p-tolyl)piperazine-1-carboxamide | 2 | 1.86 | 466.8 |

-continued

| Example | Compound Name | LCMS Method | RT | (M+) |
|---|---|---|---|---|
| 8 | 4-[2-Amino-5-(4,4-dimethyl-5H-oxazol-2-yl)thieno-[2,3-d]pyrimidin-4-yl]-N-[4-(difluoromethoxy)-phenyl]piperazine-1-carboxamide | 2 | 1.93 | 518.8 |
| 9 | 4-[2-Amino-5-(4,4-dimethyl-5H-oxazol-2-yl)thieno-[2,3-d]pyrimidin-4-yl]-N-(thien-3-yl)piperazine-1-carboxamide | 2 | 1.66 | 458.6 |
| 10 | 4-[2-Amino-5-(4,4-dimethyl-5H-oxazol-2-yl)thieno-[2,3-d]pyrimidin-4-yl]-N-(1-methylindolin-5-yl)-piperazine-1-carboxamide | 2 | 1.72 | 507.6 |
| 11 | 4-[2-Amino-5-(4,4-dimethyl-5H-oxazol-2-yl)thieno-[2,3-d]pyrimidin-4-yl]-N-(1-methylindol-5-yl)-piperazine-1-carboxamide | 2 | 1.79 | 505.8 |

General Method 7

To a solution of the appropriate hydroxy-substituted amide Intermediate (0.53 mmol) in DCM (5 mL) was added thionyl chloride (1.32 mmol) and the reaction mixture was heated at 70° C. for 2 h. The reaction mixture was then neutralized using saturated aqueous NaHCO$_3$ solution. The aqueous layer was extracted into DCM, dried over anhydrous sodium sulphate and concentrated in vacuo. To the crude residue were added methanol (5 mL) and NaOH (0.49 mmol) and the reaction mixture was stirred at 50° C. for 1 h. The reaction mixture was then concentrated and purified by column chromatography (silica 100-200 mesh, 5-10% MeOH in DCM) to afford the title compound.

General Method 8

To a solution of the appropriate hydroxy-substituted amide Intermediate (0.47 mmol) in DCM (3 mL) at −78° C. was added DAST (2.38 mmol), and the reaction mixture was stirred at −78° C. for 2 h. Solid K$_2$CO$_3$ (2.61 mmol) was added, and the reaction mixture was stirred at room temperature for 20 minutes. The reaction mixture was then diluted with water and extracted with DCM. The organic layer was dried over anhydrous sodium sulphate and concentrated in vacuo. The crude material was purified by column chromatography (100-200 mesh, 5-10% MeOH in DCM) to afford the title compound.

Examples 12 to 21

The following compounds were prepared via the indicated General Method.

| Example | Compound Name | General Method | LCMS Method | (M+) |
|---|---|---|---|---|
| 12 | 4-[2-Amino-5-(4,5-dihydrooxazol-2-yl)thieno-[2,3-d]pyrimidin-4-yl]-N-(4-methoxyphenyl)-piperazine-1-carboxamide | 7 | 3 | 454.2 |
| 13 | 4-[2-Amino-5-(4,5-dihydrooxazol-2-yl)thieno-[2,3-d]pyrimidin-4-yl]-N-(4-methoxy-2-methyl-phenyl)piperazine-1-carboxamide | 7 | 3 | 468.2 |
| 14 | 4-[2-Amino-5-(4-oxa-2-azaspiro[4.4]non-2-en-3-yl)thieno[2,3-d]pyrimidin-4-yl]-N-(4-methoxy-phenyl)piperazine-1-carboxamide | 8 | 3 | 508.2 |
| 15 | 4-[2-Amino-5-(4-oxa-2-azaspiro[4.4]non-2-en-3-yl)thieno[2,3-d]pyrimidin-4-yl]-N-(4-methoxy-2-methylphenyl)piperazine-1-carboxamide | 8 | 3 | 522.1 |
| 16 | 4-[2-Amino-5-(5-methyl-4,5-dihydrooxazol-2-yl)thieno[2,3-c/]pyrimidin-4-yl]-N-(4-methoxy-phenyl)piperazine-1-carboxamide | 7 | 3 | 468.1 |
| 17 | 4-[2-Amino-5-(5-methyl-4,5-dihydrooxazol-2-yl)thieno[2,3-d]pyrimidin-4-yl]-N-(4-methoxy-2-methylphenyl)piperazine-1-carboxamide | 7 | 3 | 482.2 |
| 18 | 4-[2-Amino-5-(5-isopropyl-4,5-dihydrooxazol-2-yl)thieno[2,3-d]pyrimidin-4-yl]-N-(4-methoxy-phenyl)piperazine-1-carboxamide | 7 | 3 | 496.2 |
| 19 | 4-[2-Amino-5-(5-isopropyl-4,5-dihydrooxazol-2-yl)thieno[2,3-d]pyrimidin-4-yl]-N-(4-methoxy-2-methylphenyl)piperazine-1-carboxamide | 7 | 3 | 510.3 |
| 20 | 4-[2-Amino-5-(4-methyl-4,5-dihydrooxazol-2-yl)thieno[2,3-d]pyrimidin-4-yl]-N-(4-methoxy-2-methylphenyl)piperazine-1-carboxamide | 7 | 3 | 482.2 |
| 21 | 4-[2-Amino-5-(4-methyl-4,5-dihydrooxazol-2-yl)thieno[2,3-d]pyrimidin-4-yl]-N-(4-methoxy-phenyl)piperazine-1-carboxamide | 7 | 3 | 468.1 |

The invention claimed is:

1. A compound of formula (I) or an N-oxide thereof, or a pharmaceutically acceptable salt or solvate thereof:

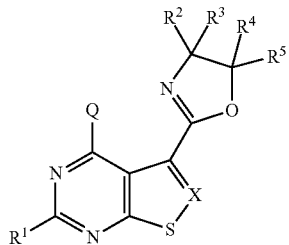

wherein
Q represents a group of formula (Qa) or (Qb):

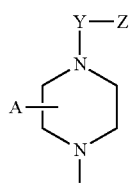

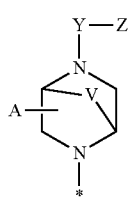

in which the asterisk (*) represents the point of attachment to the remainder of the molecule;
V represents —CH$_2$—, —C(CH$_3$)$_2$—, —CH$_2$CH$_2$— or —CH$_2$CH$_2$CH$_2$—;
X represents C—R$^6$ or N;
Y represents a covalent bond, or a linker group selected from —C(O)—, —S(O)—, —S(O)$_2$—, —C(O)O—, —C(O)N(R$^7$)— and —S(O)$_2$N(R$^7$)—;
Z represents hydrogen; or Z represents C$_{1-6}$ alkyl, C$_{3-7}$ cycloalkyl, C$_{3-7}$ cycloalkyl-(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents;
A represents hydrogen or trifluoromethyl; or A represents C$_{1-6}$ alkyl, optionally substituted by one or more substituents independently selected from halogen, —OR$^a$, —S(O)R$^a$ and —NR$^b$R$^c$;
R$^1$ represents hydrogen, halogen, cyano, nitro, hydroxy, trifluoromethyl, trifluoromethoxy, —OR$^a$, —SR$^a$, —SOR$^a$, —SO$_2$R$^a$, —NR$^b$R$^c$, —CH$_2$NR$^b$R$^c$, —NR$^c$COR$^d$, —CH$_2$NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or R$^1$ represents C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents;
R$^2$ represents hydrogen or C$_{1-6}$ alkyl; and R$^3$ represents hydrogen; or R$^3$ represents C$_{1-6}$ alkyl, C$_{1-6}$ alkoxy, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or
R$^2$ and R$^3$, when taken together with the carbon atom to which they are both attached, represent C$_{3-7}$ cycloalkyl or C$_{3-7}$ heterocycloalkyl, either of which groups may be optionally substituted by one or more substituents;
R$^4$ represents hydrogen or C$_{1-6}$ alkyl; and
R$^5$ represents hydrogen; or R$^5$ represents C$_{1-6}$ alkyl, C$_{1-6}$ alkoxy, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or
R$^4$ and R$^5$, when taken together with the carbon atom to which they are both attached, represent C$_{3-7}$ cycloalkyl or C$_{3-7}$ heterocycloalkyl, either of which groups may be optionally substituted by one or more substituents;
R$^6$ and R$^7$ independently represent hydrogen; or C$_{1-6}$ alkyl, optionally substituted by one or more substituents independently selected from —OR$^a$ and —NR$^b$R$^c$;
R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;
R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or
R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;
R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and
R$^e$ represents C$_{1-6}$ alkyl, aryl or heteroaryl, any of which groups may be optionally substituted by one or more substituents.

2. A compound as claimed in claim 1, wherein the compound of formula (I) is a compound of formula (IA), or a pharmaceutically acceptable salt or solvate thereof:

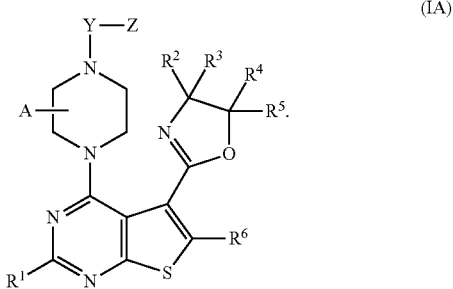

3. The compound as claimed in claim 1, wherein $R^1$ represents hydrogen or $-NR^bR^c$.

4. The compound as claimed in claim 1, wherein
$R^2$ represents hydrogen or $C_{1-6}$ alkyl; and
$R^3$ represents hydrogen or $C_{1-6}$ alkyl; or
$R^2$ and $R^3$, when taken together with the carbon atom to which they are both attached, represent $C_{3-7}$ cycloalkyl or $C_{3-7}$ heterocycloalkyl.

5. The compound as claimed in claim 1, wherein
$R^4$ represents hydrogen or $C_{1-6}$ alkyl; and
$R^5$ represents hydrogen or $C_{1-6}$ alkyl; or
$R^4$ and $R^5$, when taken together with the carbon atom to which they are both attached, represent $C_{3-7}$ cycloalkyl or $C_{3-7}$ heterocycloalkyl.

6. The compound as claimed in claim 1, wherein the compound of formula (I) is a compound of formula (IIA), or a pharmaceutically acceptable salt or solvate thereof:

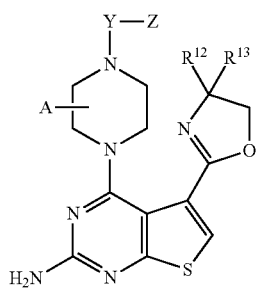

(IIA)

wherein
$R^{12}$ and $R^{13}$ independently represent hydrogen or $C_{1-6}$ alkyl.

7. The compound as claimed in claim 1, wherein the compound of formula (I) is a compound of formula (IIB), or a pharmaceutically acceptable salt or solvate thereof:

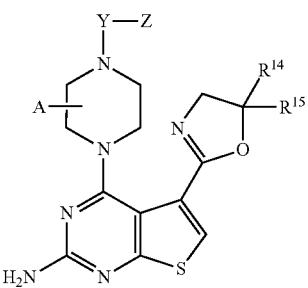

(IIB)

wherein
$R^{14}$ and $R^{15}$ independently represent hydrogen or $C_{1-6}$ alkyl.

8. The compound as claimed in claim 1, wherein the compound of formula (I) is a compound of formula (IIC), or a pharmaceutically acceptable salt or solvate thereof:

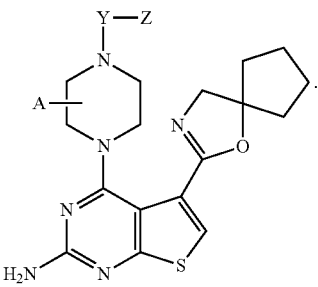

(IIC)

9. The compound as claimed in claim 1, wherein Y represents $-C(O)N(R^7)$.

10. The compound as claimed in claim 1, wherein Z represents aryl, $C_{3-7}$ heterocycloalkyl or heteroaryl, any of which groups may be optionally substituted by one or two substituents independently selected from halogen, cyano, $C_{1-6}$ alkyl, $C_{1-6}$ alkoxy, difluoromethoxy, $C_{2-6}$ alkylcarbonyl and $C_{2-6}$ alkoxy-carbonyl.

11. The compound as claimed in claim 1, wherein A represents hydrogen; or A represents $C_{1-6}$ alkyl, optionally substituted by $-OR^a$.

12. A pharmaceutical composition comprising a compound according to claim 1 or an N-oxide thereof, or a pharmaceutically acceptable salt or solvate thereof, in association with a pharmaceutically acceptable carrier.

13. A method for treating organ or cell transplant rejection, which comprises administering to a patient in need of such treatment an effective amount of a compound according to claim 1 or an N-oxide thereof, or a pharmaceutically acceptable salt or solvate thereof.

14. The compound according to claim 1 that is
4-[2-Amino-5-(4,4-dimethyl-5H-oxazol-2-yl)thieno[2,3-d]pyrimidin-4-yl]piperazine-1-carboxylic acid (4-methoxy-2-methylphenyl)amide;
4-[2-Amino-5-(4,4-dimethyl-5H-oxazol-2-yl)thieno-[2,3-d]pyrimidin-4-yl]-N-(4-methoxyphenyl)-piperazine-1-carboxamide;
4-[2-Amino-5-(4,4-dimethyl-5H-oxazol-2-yl)thieno-[2,3-d]pyrimidin-4-yl]-N-(2-fluoro-4-iodophenyl)-piperazine-1-carboxamide;
4-[2-Amino-5-(4,4-dimethyl-5H-oxazol-2-yl)thieno-[2,3-d]pyrimidin-4-yl]-N-(2-cyanophenyl)piperazine-1-carboxamide;
Ethyl 4-({4-[2-amino-5-(4,4-dimethyl-5H-oxazol-2-yl)thieno[2,3-d]pyrimidin-4-yl]piperazine-1-carbonyl}amino)benzoate;
N-(4-Acetylphenyl)-4-[2-amino-5-(4,4-dimethyl-5H-oxazol-2-yl)thieno[2,3-d]pyrimidin-4-yl]piperazine-1-carboxamide;
4-[2-Amino-5-(4,4-dimethyl-5H-oxazol-2-yl)thieno-[2,3-d]pyrimidin-4-yl]-N-(p-tolyl)piperazine-1-carboxamide;
4-[2-Amino-5-(4,4-dimethyl-5H-oxazol-2-yl)thieno-[2,3-d]pyrimidin-4-yl]-N-[4-(difluoromethoxy)-phenyl]piperazine-1-carboxamide;
4-[2-Amino-5-(4,4-dimethyl-5H-oxazol-2-yl)thieno-[2,3-d]pyrimidin-4-yl]-N-(thien-3-yl)piperazine-1-carboxamide;
4-[2-Amino-5-(4,4-dimethyl-5H-oxazol-2-yl)thieno-[2,3-d]pyrimidin-4-yl]-N-(1-methylindolin-5-yl)-piperazine-1-carboxamide;

4-[2-Amino-5-(4,4-dimethyl-5H-oxazol-2-yl)thieno-[2,3-d]pyrimidin-4-yl]-N-(1-methylindol-5-yl)-piperazine-1-carboxamide;

4-[2-Amino-5-(4,5-dihydrooxazol-2-yl)thieno-[2,3-d]pyrimidin-4-yl]-N-(4-methoxyphenyl)-piperazine-1-carboxamide;

4-[2-Amino-5-(4,5-dihydrooxazol-2-yl)thieno-[2,3-d]pyrimidin-4-yl]-N-(4-methoxy-2-methyl-phenyl)piperazine-1-carboxamide;

4-[2-Amino-5-(4-oxa-2-azaspiro[4.4]non-2-en-3-yl)thieno[2,3-d]pyrimidin-4-yl]-N-(4-methoxy-phenyl)piperazine-1-carboxamide;

4-[2-Amino-5-(4-oxa-2-azaspiro[4.4]non-2-en-3-yl)thieno[2,3-d]pyrimidin-4-yl]-N-(4-methoxy-2-methylphenyl)piperazine-1-carboxamide;

4-[2-Amino-5-(5-methyl-4,5-dihydrooxazol-2-yl)thieno[2,3-d]pyrimidin-4-yl]-N-(4-methoxy-phenyl)piperazine-1-carboxamide;

4-[2-Amino-5-(5-methyl-4,5-dihydrooxazol-2-yl)thieno[2,3-d]pyrimidin-4-yl]-N-(4-methoxy-2-methylphenyl)piperazine-1-carboxamide;

4-[2-Amino-5-(5-isopropyl-4,5-dihydrooxazol-2-yl)thieno[2,3-d]pyrimidin-4-yl]-N-(4-methoxy-phenyl)piperazine-1-carboxamide;

4-[2-Amino-5-(5-isopropyl-4,5-dihydrooxazol-2-yl)thieno[2,3-d]pyrimidin-4-yl]-N-(4-methoxy-2-methylphenyl)piperazine-1-carboxamide;

4-[2-Amino-5-(4-methyl-4,5-dihydrooxazol-2-yl)thieno[2,3-d]pyrimidin-4-yl]-N-(4-methoxy-2-methylphenyl)piperazine-1-carboxamide;

4-[2-Amino-5-(4-methyl-4,5-dihydrooxazol-2-yl)thieno[2,3-d]pyrimidin-4-yl]-N-(4-methoxy-phenyl)piperazine-1-carboxamide;

or an N-oxide thereof, or a pharmaceutically acceptable salt or solvate thereof.

* * * * *